United States Patent [19]
Drenthen

[11] Patent Number: 5,546,812
[45] Date of Patent: Aug. 20, 1996

[54] METHOD AND DEVICE FOR DETERMINING CHARACTERISTICS OF THE FLOW OF A MEDIUM

[75] Inventor: Jan G. Drenthen, Mijnsheerenland, Netherlands

[73] Assignee: Servex B.V., Dordrecht, Netherlands

[21] Appl. No.: 291,146

[22] Filed: Aug. 16, 1994

[30] Foreign Application Priority Data

Aug. 17, 1993 [NL] Netherlands ................. 9301422

[51] Int. Cl.⁶ ........................................ G01F 1/66
[52] U.S. Cl. .................... 73/861.29; 73/861.28; 73/861.31
[58] Field of Search ............... 73/861.29, 861.28, 73/861.31, 861.29

[56] References Cited

U.S. PATENT DOCUMENTS

| | | | |
|---|---|---|---|
| 3,729,995 | 5/1973 | Kovacs et al. | 73/861.03 |
| 3,940,985 | 3/1976 | Wyler | 73/861.31 |
| 4,078,428 | 3/1978 | Baker et al. | 73/861.31 |
| 4,102,186 | 7/1978 | Brown | 73/861.31 |
| 4,286,470 | 9/1981 | Lynnworth | 73/861.18 |
| 4,300,400 | 11/1981 | Bistrian, Jr. et al. | 73/861.28 |
| 4,610,167 | 9/1986 | McShane | 73/861.28 |
| 4,646,575 | 3/1987 | O'Hair et al. | 73/861.31 |
| 4,831,884 | 5/1989 | Drenthen | 73/861.27 |
| 4,930,350 | 6/1990 | Motegi et al. | 73/861.28 |
| 5,372,047 | 12/1994 | Russwurm et al. | 73/861.29 |
| 5,392,645 | 2/1995 | Kleppe | 73/861.28 |
| 5,437,194 | 8/1995 | Lynnworth | 73/861.27 |
| 5,477,734 | 12/1995 | Zemel et al. | 73/204.23 |

*Primary Examiner*—Richard Chilcot
*Assistant Examiner*—Jewel V. Arxis
*Attorney, Agent, or Firm*—Deveau, Colton & Marquis

[57] ABSTRACT

The invention relates to a method for determining characteristic of the flow of a medium in a channel by measuring the transit times of sound waves which are transmitted between one or more transducers, and determining the characteristics from the measured transit times.

In one embodiment of the method according to the invention, at least two sound waves whose transit times depend on swirl are transmitted along acoustic paths with a different sensitivity to swirl, and a measure of the swirl is determined from the measured transit times.

In another embodiment, at least two sound waves whose transit times depend on the symmetry of the flow profile are transmitted along acoustic paths with a different sensitivity to symmetry, and a measure of the symmetry is determined from the measured transit times.

These embodiments are preferably combined.

If weighting factors are allocated to the values obtained, the individual velocities of the sound waves can be used to calculate the average flow velocity and/or the throughput of the medium. Since allowance is made for possible disturbances of the velocity profile, the accuracy of the calculated variables is good.

The invention also provides for a device, by means of which the method according to the invention can be carried out.

19 Claims, 1 Drawing Sheet

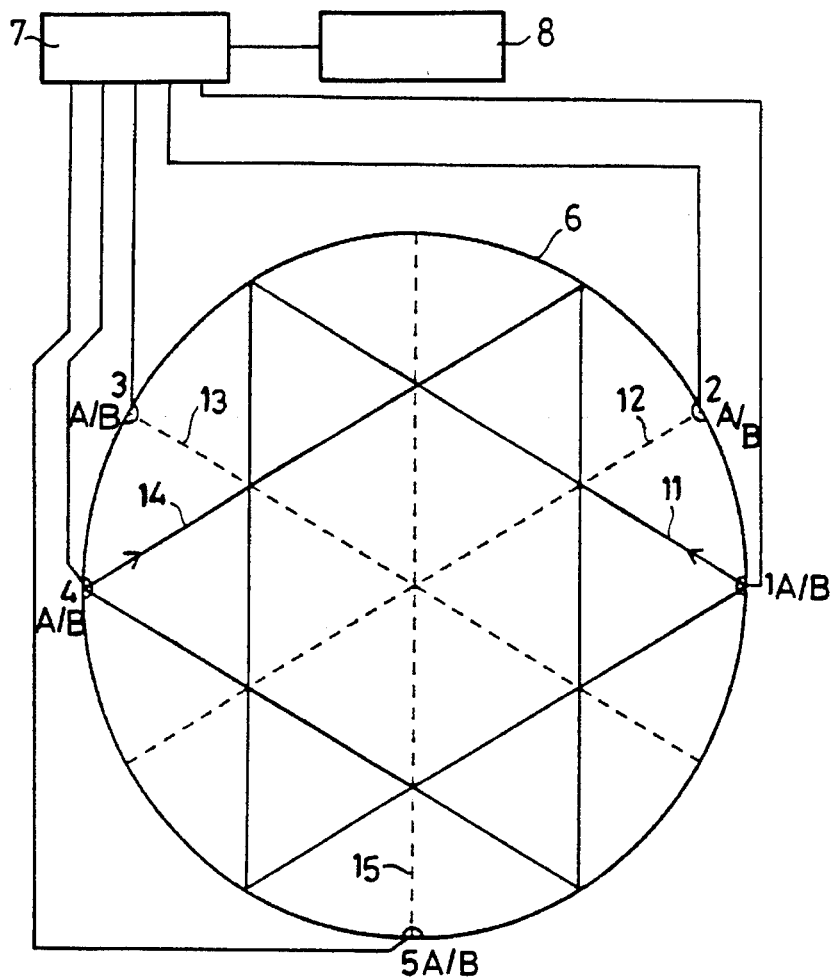
FIG. 1.
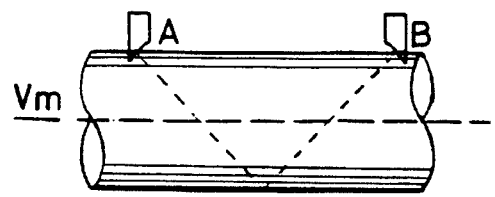 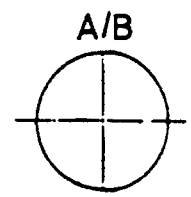
FIG. 2.A   FIG. 2.B
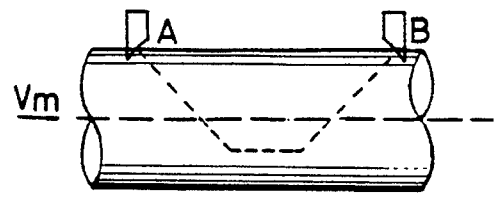 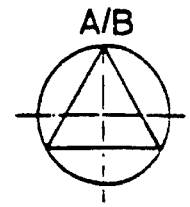
FIG. 3.A   FIG. 3.B

METHOD AND DEVICE FOR DETERMINING CHARACTERISTICS OF THE FLOW OF A MEDIUM

BACKGROUND OF THE INVENTION

The present application relates to a method for determining characteristics of the flow of a medium in a channel by transmitting and receiving sound waves along one or more acoustic paths using one or more acoustic transducers, each of which can act individually as a transmitter and receiver, and by measuring the transit times of the transmitted sound waves, and determining flow characteristics from the measured transit times.

Such a method is generally known. It involves determining the average flow velocity and/or the throughput of the medium from the difference in transit time of sound waves which are transmitted in the downstream direction and upstream direction respectively between acoustic transducers set up at a distance from each other. The medium can be a gas or liquid.

The transit times of the sound waves not only depend on the flow velocity of the medium, but are also influenced by the flow profile of the medium. In a flowing medium, apart from the longitudinal movement, a swirl can occur. Other possible disturbances of the ideal flow profile are a flow velocity fluctuating in time and a flow profile which is asymmetrical relative to the longitudinal axis. Such disturbances occur in particular in pipe systems which have a complex structure.

The ultimate reliability of the calculated flow velocity of the medium depends on the distance covered, the acoustic path, on the transmitted sound wave, and on the calculation method used. Many configurations are known for the acoustic path.

In the case of the conventional methods which are used in commercially available measuring instruments, several acoustic paths are used, running parallel to each other. The known numerical Gaussian square method is used for positioning of the paths and the various weighting factors which are allocated to the measured velocities.

The advantages of this method are clear. No additional information on the flow profile is required for calculating the velocity. The weighting factors are fixed in advance, so that the microprocessor which is used for calculation of the characteristics need only carry out a limited number of calculations.

Although this means that measurement of the flow velocity is simple to carry out and excellent results can be obtained in ideal flow conditions, the method has a number of clear disadvantages, due to the underlying assumptions and limitations of the Gaussian integration method. These underlying assumptions and limitations are as follows:

It is assumed that the flow profile is fully axially symmetrical.

No additional information from the Reynolds number is used.

As a result of the fixed weighting factors for the various acoustic paths, which are optimized for the undisturbed flow profile, errors will occur when the actual flow profile deviates from the ideal profile.

OBJECTS OF THE INVENTION

The object of the present invention is to provide a method for determining characteristics of the flow of a medium in a channel, such as swirl and symmetry.

Another object of the present invention is to provide a method for determining the flow velocity and/or throughput of a medium in a channel with more accurate results, due to the fact that errors caused by disturbances of the ideal flow profile are eliminated.

SUMMARY OF THE INVENTION

The method according to the invention of the abovementioned type is characterized in that at least two sound waves whose transit times depend on swirl are transmitted along acoustic paths with a different sensitivity to swirl, and a measure of the swirl in the flow is determined from the measured transit times.

DETAILED DESCRIPTION OF THE INVENTION

In the case of this method, sound waves are transmitted along acoustic paths with a different sensitivity to swirl.

Firstly, this can mean that a first sound wave is transmitted in a stationary medium in a plane at right angles to the direction of flow (the sensitivity to swirl is zero at this so-called calibration standard), and a second sound wave is then transmitted along the same acoustic path in a flowing medium, in which the sensitivity to swirl is different.

Secondly, this can mean that sound waves are transmitted along different acoustic paths which are sensitive to swirl, in the same direction of flow of the flowing medium, either downstream or upstream.

A measure of the swirl can be determined from comparison of the measured transit times of the transmitted sound waves along acoustic paths with a different sensitivity to swirl. If the measured transit times are identical, there is no swirl. If the measured transit times are not identical, the difference in the transit times is a measure of the intensity of the swirl. This measure of the intensity contains both the magnitude and the direction of the swirl.

The channel in which the method is carried out will in many cases be a cylindrical pipe, but the method can also be used in channels of other shapes, such as a square cross-section or a U-shaped channel.

The method can be used advantageously in a cylindrical pipe through sound waves whose transit times depend on swirl being transmitted along various acoustic paths with at least two reflections against the wall of the channel, and at least one sound wave being transmitted clockwise and at least one sound wave in a direction opposite thereto. The sound waves, two reflections of which are taken up in the acoustic path, traverse a large part of the cross-section of the channel and thus give a reliable picture of the flow.

Another embodiment of the acoustic path of sound waves whose transit time depends on swirl is an acoustic path without reflection against the wall of the channel.

The invention also relates to a method of the abovementioned type which is characterized in that at least two sound waves whose transit times depend on the symmetry of the flow profile are transmitted along acoustic paths with a different sensitivity to symmetry, and a measure of the symmetry of the flow profile is determined from the measured transit times thereof.

In the case of this method, sound waves are transmitted along acoustic paths which are sensitive to asymmetrical flow profiles. In a similar way to that described above for determining a measure of the swirl, a measure of the symmetry can be derived from the difference in transit time of said sound waves.

The above-described methods are advantageously combined by transmitting both sound waves whose transit times depend on swirl along acoustic paths with a different sensitivity to swirl and sound waves whose transit times depend on symmetry along acoustic paths with a different sensitivity to symmetry, and determining a measure of the swirl in the flow and a measure of the symmetry of the flow profile from the measured transit times.

The sound waves whose transit times depend on the symmetry of the flow profile are preferably transmitted along different acoustic paths with one reflection against the wall of the channel, in which case the acoustic paths cross the longitudinal axis of the channel. Such sound waves are preferably transmitted along three different acoustic paths, so that the sound waves traverse the entire cross-section of the channel.

The method according to the invention first of all gives an insight into the possible presence and magnitude of disturbances of the ideal flow profile, such as swirl and asymmetry.

If the transit times of sound waves along the various acoustic paths in a stationary flow are known, for example by means of calibration, the average flow velocity and/or the throughput of the medium can be calculated from the difference in transit time of sound waves in a stationary and flowing medium respectively along the same acoustic path.

However, prior calibration is not necessary. For this purpose, two sound waves are advantageously transmitted along an acoustic path in the downstream and upstream direction respectively. Two sound waves are preferably transmitted along each acoustic path in the downstream and upstream direction respectively. The average flow velocity can be determined from the difference in transit time of sound waves transmitted along the same acoustic path, but in opposite directions of flow.

In order also to detect the presence of a flow which fluctuates in time, several sound waves are preferably transmitted in rapid succession along the same acoustic path, and a measure of the pulsation of the flow of the medium is determined from the measured transit times thereof. The difference in transit time of two sound waves transmitted in rapid succession along the same acoustic path is a measure of the fluctuation in time of the flow of the medium.

A weighting factor is advantageously allocated to the measure of a characteristic, and by means thereof and the individual velocities along the various acoustic paths the flow velocity and/or the throughput of the medium in the channel is determined.

The method is preferably carried out by allocating weighting factors to the measure of swirl and symmetry, and if desired the pulsation, and by means thereof and the individual velocities along the various acoustic paths calculating the flow velocity and/or the throughput of the medium in the channel. Since account is taken of possible disturbances when calculating the flow velocity and/or the throughput of the medium, a reliable value is obtained for them. The Reynolds number is advantageously involved in the calculation of the flow velocity and/or the throughput of the medium. The accuracy of such a measurement is better than 0.3% of the calculated value for flow velocities of 0.3 to 30 m/s (1 to 100 foot/sec).

The individual velocities along the various acoustic paths can be determined either by a prior calibration or by measuring the transit times of sound waves transmitted along the same acoustic path in the downstream and upstream directions respectively, as described above.

Measurements by means of the method according to the invention can be carried out simply in complex pipe systems, without the flow of the medium having to be evened out by flow elements or other aids.

The present invention also relates to a device for determining characteristics of the flow of a medium in a channel, which device comprises one or more acoustic transducers, each of which can act individually as a transmitter and receiver for transmitting sound waves along acoustic paths and receiving thereof, and means for measuring the transit time of the transmitted sound waves, and means for determining the characteristics from the measured transit times. Such a device is also generally known from the prior art.

The device according to the invention is characterized in that the device comprises at least two pairs of acoustic transducers, in which the transducers transmit a sound wave whose transit time depends on swirl along acoustic paths with a different sensitivity to swirl, and the means for determining the characteristics from the measured transit times determine a measure of the swirl.

The transducers transmitting sound waves whose transit times depend on swirl advantageously transmit sound waves along acoustic paths with at least two reflections against the wall of the channel, and at least one sound wave thereof is in the clockwise direction, while at least one sound wave is in the opposite direction. In another embodiment of the device according to the invention, the transducers transmitting sound waves whose transit times depend on swirl transmit sound waves along acoustic paths without reflection against the wall of the channel.

Another embodiment of the device of the above-mentioned type according to the invention is characterized in that the device has at least two pairs of transducers, in which the transducers transmit sound waves whose transit times depend on the symmetry of the flow profile along acoustic paths with a different sensitivity to symmetry, and the means for determining the characteristics from the measured transit times determine a measure of the symmetry of the flow profile.

In a preferred embodiment of the device according to the invention, the device comprises at least two pairs of acoustic transducers, in which the transducers transmit sound waves whose transit times depend on swirl along acoustic paths with a different sensitivity to swirl and at least two pairs of transducers, in which the transducers transmit sound wave whose transit times depend on the symmetry of the flow profile along acoustic paths with a different sensitivity to symmetry, and the means for determining the characteristics from the measured transit times determine a measure of the swirl and a measure of the symmetry of the flow profile.

With these devices according to the invention an insight can be gained into the type of flow of the medium.

The transducers which transmit sound waves whose transit times depend on the symmetry of the flow profile expediently transmit sound waves along various acoustic paths with one reflection against the wall of the channel, which acoustic paths cross the longitudinal axis of the channel. The device is preferably provided with three pairs of such transducers, so that the sound waves which are transmitted along the various acoustic paths scan the entire cross-section of the channel.

A pair of transducers advantageously sends two sound waves along the same acoustic path in the downstream direction and upstream direction respectively, so that the means for determining the characteristics from the measured transit times can determine the flow velocity along said acoustic path. Each pair of transducers preferably transmits sound waves along each acoustic path in the down-stream direction and upstream direction respectively.

In order also to determine the measure of pulsation of the flow with the device according to the invention, the transducers can be designed to transmit several sound waves in rapid succession along the same acoustic path, and the means for determining the characteristics from the measured transit times also determine a measure of the pulsation.

In order to permit use of the device as a flowmeter, the means for determining the characteristics calculate the flow velocity and/or the throughput of the medium from the measure of a characteristic and the individual velocities along the various acoustic paths.

The means for determining the characteristics advantageously calculate the flow velocity and/or the throughput of the medium from the measure of the swirl and symmetry, and if desired the pulsation and the individual velocities, along the various acoustic paths.

BRIEF DESCRIPTION OF THE DRAWING

The invention will be explained in greater detail below with reference to the appended drawing, in which:

FIG. 1 is a projection of various acoustic paths of the transmitted sound waves according to the invention;

FIG. 2B is a side view of an acoustic path with a single reflection;

FIG. 3A is a view of an acoustic path with a double reflection.

DESCRIPTION OF THE PREFERRED EMBODIMENT

FIG. 1 shows a configuration of acoustic paths of the sound waves according to a preferred embodiment of the invention. In the situation shown, the channel is a cylindrical pipe 6. The reference numbers 1A/B to 5A/B indicate pairs of transducers set up at a distance from each other, which transducers can act as transmitters and receivers. The transducers 1A and 4A transmit sound waves (indicated by a solid line) along various acoustic paths with two reflections, a sound wave 11 being transmitted in an anticlockwise direction, and a sound wave 14 in a clockwise direction. The acoustic paths of the sound waves 11 and 14 have a different sensitivity to swirl in the flow. The transmitted sound waves are received by the transducers 1B and 4B respectively. Said transducers 1B and 4B themselves transmit sound waves (not shown) in the opposite direction along the acoustic paths with two reflections, which sound waves are received by the transducers 1A and 4A. The transmitted sound waves 11 and 14 and the sound waves transmitted in the opposite direction traverse a large part of the cross-section of the channel 6. The transit time of the sound waves between the transducers depends on swirl.

The transducers 2A, 3A and 5A transmit sound waves 12, 13 and 15 respectively (shown by a dashed line) with a single reflection against the wall of the channel 6. The acoustic paths of the sound waves 12, 13 and 15 have a different sensitivity to the symmetry of the flow profile. The transducers 2B, 3B and 5B receive said sound waves and themselves transmit sound waves in the opposite direction along different acoustic paths. The sound waves cross the longitudinal axis of the channel 6. The transit time of said sound waves depends on the symmetry of the flow.

Reference number 7 indicates diagrammatically means for measuring the transit time of the sound waves. Said means 7 are connected to the transmitters and receivers. Means 8 for determining the characteristics of the flow, such as the intensity of the swirl and asymmetry of the flow profile, are also shown diagrammatically.

FIGS. 2 and 3 show acoustic paths with a single and double reflection respectively between a transmitter A and receiver B. The arrow $v_m$ indicates the direction of flow of the medium.

Examples of the interpretation and processing of the measured transit times of sound waves with acoustic paths, as shown in FIG. 1, are given below.

The results are presented in the form of a matrix. The table below is an example of such a matrix.

TABLE 1

| | | Identical | | |
| --- | --- | --- | --- | --- |
| | | Yes | | No |
| | | Low | Average | High |
| Paths sensitive to symmetry | Fluctuations | Yes | | |
| | | No | | |
| Paths sensitive to swirl | Fluctuations | Yes | | |
| Reynolds number | | No | | |

The transit times of the sound waves transmitted in the same direction of flow along different acoustic paths which are sensitive to symmetry are compared. If there are deviations, a distinction is made in the size of the differences measured. The deviations are broken down into one or more of three categories, namely low, average and high. This means that in that case a low, average and high deviation of the symmetry in the flow is present. Of course, more or fewer categories may be used if desired.

The transit times of the sound waves which are sensitive to swirl of the flow are also compared and, if there are deviations, they are broken down into one of the three categories.

For each type of sound wave it is also ascertained whether the flow velocity fluctuates in time.

The flow velocity of the medium is also calculated for each acoustic path from the difference in transit time of sound waves which are transmitted along the same acoustic path in the downstream and upstream direction.

The flow velocity and/or the throughput are calculated with the aid of this matrix and weighting factors to be allocated to it and the individual velocities along the various acoustic paths.

EXAMPLES

Two examples of flow profiles and the corresponding matrix are given below.

Example 1

In Table 2 below the flow behaviour of a medium with an ideal flow profile is characterized. In this table "0" means absent and "X" means present.

TABLE 2

| | | | Identical | | |
| | | | Yes | | No |
| | | | Low | Average | High |
|---|---|---|---|---|---|
| Paths sensitive to symmetry | Fluctuations | Yes | 0 | 0 | 0 | 0 |
| | | No | X | 0 | 0 | 0 |
| Paths sensitive to swirl | Fluctuations | Yes | 0 | 0 | 0 | 0 |
| | | No | X | 0 | 0 | 0 |
| Reynolds number | | | X | 0 | 0 | 0 |

In an ideal flow profile there are no differences in the transit times of sound waves (downstream or upstream) along similar acoustic paths, and no fluctuations of the flow velocity in time occur.

Example 2

Table 3 below shows the behaviour of a medium after a double bend in a compressor station.

TABLE 3

Flow profile after a double bend in a compressor station

| | | | Identical | | |
| | | | Yes | | No |
| | | | Low | Average | High |
|---|---|---|---|---|---|
| Paths sensitive to symmetry | Fluctuations | Yes | X | 0 | X | X |
| | | No | 0 | 0 | 0 | 0 |
| Paths sensitive to swirl | Fluctuations | Yes | 0 | 0 | X | X |
| | | No | X | 0 | 0 | 0 |
| Reynolds number | | | X | 0 | X | X |

As can be seen from Table 3, the flow profile of a medium after a double bend in a compressor station is disturbed. Both asymmetry and swirl occur, so that the symmetry of the flow changes in time. From the measured transit times an average to high value is allocated to the intensity of the disturbance. The Reynolds number is also influenced by these disturbances.

If weighting factors are allocated to the disturbances occurring, said weighting factors and the individual velocities along the acoustic paths can be used to calculate the average flow velocity and from it the throughput.

What is claimed is:

1. A method for determining swirl of a flow of a medium in a conduit by transmitting and receiving at least two sound waves along first acoustic paths with different sensitivities to swirl using at least one acoustic transducer, which can act individually as a transmitter and receiver, the first acoustic paths comprising at least one reflection against the wall of the conduit, and by measuring the transit times of the transmitted sound waves and determining a measure of swirl from the measured transit times.

2. The method according to claim 1, wherein the first acoustic paths comprise at least two reflections against the wall of the conduit, and at least one sound wave is transmitted clockwise within the conduit and at least one sound wave in a direction opposite thereto.

3. The method according to claim 1, wherein also at least two sound waves are transmitted and received along second acoustic paths having different sensitivities to symmetry, the second acoustic paths comprising one reflection against the wall of the conduit and crossing the longitudinal axis of the conduit, and the transit times of the transmitted sound waves are measured to determine a measure of the symmetry of the flow profile.

4. The method according to claim 3 wherein the sound waves whose transit times depend on the symmetry of the flow profile are transmitted along three different acoustic paths, each having one reflection against the wall of the conduit and crossing the longitudinal axis of the conduit.

5. The method according to claim 3, wherein two sound waves are transmitted along each acoustic path, one in the downstream direction and one in the upstream direction.

6. The method according to claim 3, wherein several sound waves are transmitted in rapid succession along the same acoustic path, and a measure of pulsation of the flow of the medium is determined from the measured transit times thereof.

7. The method according to claim 3, wherein weighting factors are allocated to the measures of swirl and symmetry, and by means thereof and the individual velocities along the various acoustic paths the throughput of the medium in the conduit is calculated.

8. The method according to claim 6, wherein weighting factors are allocated to the measures of swirl, symmetry and pulsation, and by means thereof and the individual velocities along the various acoustic paths the throughput of the medium in the conduit is calculated.

9. The method according to claim 8, wherein the Reynolds number is involved in the calculation of the throughput of the medium.

10. A method for determining symmetry of a flow of a medium in a conduit by transmitting and receiving at least two sound waves along acoustic paths with different sensitivities to symmetry using at least one acoustic transducer, which can act individually as a transmitter and receiver, the acoustic paths comprising one reflection against the wall of the conduit and crossing the longitudinal axis of the conduit, and by measuring the transit times of the transmitted sound waves and determining a measure of the symmetry of the flow profile from the measured transit times.

11. A device for determining swirl of a flow of a medium in a conduit, comprising at least one acoustic transducer, which can act individually as a transmitter and receiver for transmitting sound waves along first acoustic paths having different sensitivities to swirl and receiving thereof, said at least one transducer being arranged at the periphery of the conduit in such a way that the first acoustic paths comprise at least one reflection against the wall of the conduit, as well as means for measuring transit times of the sound waves and determining a measure of swirl from the measured transit times.

12. The device according to claim 11, wherein at least two pairs of transducers are provided, the first acoustic paths thereof comprising at least two reflections against the wall of the conduit and the direction of the sound waves between one transducer pair is opposite to the direction of the sound waves between the other transducer pair.

13. The device according to claim 11, also comprising at least one acoustic transducer, which can act individually as a transmitter and receiver for transmitting sound waves along second acoustic paths having different sensitivities to symmetry and receiving thereof, which transducer is arranged at the periphery of the conduit in such a way that the second acoustic paths comprise one reflection against the wall of the conduit thereby crossing the longitudinal axis of the conduit, as well as means for determining a measure of symmetry from the measured transit times.

14. A device according to claim 13, wherein three pairs of transducers are provided, the individual transducers of which transmit sound waves whose transit times depend on the symmetry of the flow profile along various acoustic paths.

15. A device according to claim 13, wherein the transducers are in relative upstream-downstream positions at the periphery of the conduit.

16. A device according to claim 13, wherein the transducers are designed to transmit several sound waves in rapid succession in the same direction along the same acoustic path, the device further comprising means for determining a measure of pulsation of the flow.

17. A device according to claim 13, wherein the means for determining the swirl and symmetry calculate throughput of the medium from the measure of the swirl and symmetry and the individual velocities along the various acoustic paths.

18. A device according to claim 16, wherein the means for determining the swirl, symmetry and pulsation calculate throughput of the medium from the measures of swirl, symmetry and pulsation and the individual velocities along the various acoustic paths.

19. A device for determining symmetry of a flow profile of a medium in a conduit, comprising at least one acoustic transducer, which can act individually as a transmitter and receiver for transmitting sound waves along acoustic paths having different sensitivities to symmetry and receiving thereof, which at least one transducer is arranged in the periphery of the conduit in such a way that the acoustic paths comprise one reflection against the wall of the conduit thereby crossing the longitudinal axis of the conduit, as well as means for measuring transit times of the sound waves and determining a measure of symmetry from the measured transit times.

\* \* \* \* \*